US008574516B2

(12) United States Patent
Teng et al.

(10) Patent No.: US 8,574,516 B2
(45) Date of Patent: Nov. 5, 2013

(54) APPARATUS FOR INSULATED ISOTHERMAL POLYMERASE CHAIN REACTION

(75) Inventors: Ping-Hua Teng, Taichung (TW); Cheng Su, Taichung (TW)

(73) Assignee: Genereach Biotechnology Corp., Taichung (TW)

( * ) Notice: Subject to any disclaimer, the term of this patent is extended or adjusted under 35 U.S.C. 154(b) by 0 days.

(21) Appl. No.: 13/324,383

(22) Filed: Dec. 13, 2011

(65) Prior Publication Data

US 2012/0244048 A1 Sep. 27, 2012

(30) Foreign Application Priority Data

Mar. 22, 2011 (TW) ............................ 100109780 A

(51) Int. Cl.
*B01L 9/06* (2006.01)
*C12M 1/36* (2006.01)
*C12M 1/38* (2006.01)
*C12M 3/00* (2006.01)

(52) U.S. Cl.
USPC ......................... 422/562; 435/286.2; 435/809

(58) Field of Classification Search
USPC ....................................... 422/562; 435/286.2
See application file for complete search history.

(56) References Cited

U.S. PATENT DOCUMENTS

| | | | | |
|---|---|---|---|---|
| 5,616,301 | A * | 4/1997 | Moser et al. | 422/64 |
| 5,720,406 | A * | 2/1998 | Fassbind et al. | 220/23.4 |
| 5,935,524 | A * | 8/1999 | Bass et al. | 422/562 |
| 6,004,513 | A * | 12/1999 | Albagli et al. | 422/68.1 |
| 6,197,572 | B1 * | 3/2001 | Schneebeli | 435/286.2 |
| 6,403,037 | B1 * | 6/2002 | Chang et al. | 422/68.1 |
| 6,472,186 | B1 * | 10/2002 | Quintanar et al. | 435/91.2 |
| 6,638,761 | B2 * | 10/2003 | Shin et al. | 435/288.4 |
| 6,677,151 | B2 * | 1/2004 | Sandell | 435/287.2 |
| 7,081,600 | B2 * | 7/2006 | Brown et al. | 219/428 |
| 7,133,726 | B1 * | 11/2006 | Atwood et al. | 700/1 |
| 7,255,833 | B2 * | 8/2007 | Chang et al. | 422/417 |

* cited by examiner

*Primary Examiner* — Neil N Turk
*Assistant Examiner* — Brittany Fisher
(74) *Attorney, Agent, or Firm* — Muncy, Geissler, Olds & Lowe, PLLC

(57) ABSTRACT

An apparatus for holding a test tube in which insulated isothermal polymerase chain reaction is performed includes a heat sink and a tube rack. The heat sink has a main body with a through hole for insertion of the test tube. The through hole has a relatively big diameter section and a relatively small diameter section located below the relatively big diameter section. The tube rack is mounted on the heat sink for insertion of the test tube. The apparatus can ensure that the temperature at the liquid level of the reaction mixture is lower than the temperature suitable for conducting the primer annealing step in the polymerase chain reaction process.

5 Claims, 2 Drawing Sheets

APPARATUS FOR INSULATED ISOTHERMAL POLYMERASE CHAIN REACTION

BACKGROUND OF THE INVENTION

1. Field of the Invention

The present invention relates generally to apparatuses for use in polymerase chain reaction (hereinafter referred to as "PCR") and more particularly, to an apparatus for holding a test tube for insulated isothermal PCR.

2. Description of the Related Art

In the filed of biotechnology, polymerase chain reaction (PCR) is a well-known technology used to amplify specific nucleic acid sequences. The PCR process comprises three major steps including denaturation, primer annealing and extension, which require different reaction temperatures. The required temperature for the denaturation step is typically in a range between 90° C. and 97° C. The required temperature for the primer annealing step will depend on the melting temperature of the primer used. Typically, the annealing temperature ranges from 35° C. to 65° C. The required temperature for the extension step is typically about 72° C.

The insulated isothermal PCR is based on Rayleigh-Bénard convection, which is driven by buoyancy when heating fluid layer from below, is a common physical phenomenon. The insulated isothermal PCR is generally performed by immersing the bottom of a test tube which contains a reaction mixture into a hot water in such a way that the rest portion of the test tube is exposed to atmosphere at room temperature for heat dissipation. As a result, the temperature of the reaction mixture will gradually decrease from the bottom of the reaction mixture having a temperature of about 97° C. toward the liquid level of the reaction mixture having a temperature of about 35° C. Because of the temperature gradient, the heat convection is induced, such that the reaction mixture will flow through various regions having different temperatures and then undergo different reaction steps.

In the conventional apparatus for performing a convection PCR, because the portion of the test tube, which is exposed to the ambient air at room temperature for heat dissipation, has a low heat dissipating rate, the temperature at the liquid level of the reaction mixture will become higher and higher due to the increment of the heating time. As a result, the temperature at the liquid level of the reaction mixture may rise to a degree higher than the required temperature suitable for conducting the primer annealing step before the convection PCR has been performed completely. Under this circumstance, the polymerase chain reaction may break, such that a desired, large amount of copies of specific nucleic acid sequences may not be obtained.

SUMMARY OF THE INVENTION

The present invention has been accomplished in view of the above-noted circumstances. It is the primary objective of the present invention to provide an apparatus for insulated isothermal PCR, which can ensure that the temperature at the liquid level of the reaction mixture is lower than the temperature suitable for conducting the primer annealing step in the PCR process.

To achieve the above-mentioned objective, the apparatus provided by the present invention is adapted for holding a test tube in which a insulated isothermal polymerase chain reaction is performed, which comprises a heat sink having a main body provided with a through hole for insertion of the test tube. The through hole has a relatively big diameter section and a relatively small diameter section located below the relatively big diameter section. By means of the design of the present invention, the temperature at the liquid level of the reaction mixture can be kept in a degree lower than the temperature suitable for conducting the primer annealing step in the PCR process.

BRIEF DESCRIPTION OF THE DRAWINGS

The present invention will become more fully understood from the detailed description given herein below and the accompanying drawings which are given by way of illustration only, and thus are not limitative of the present invention, and wherein.

DETAILED DESCRIPTION OF THE INVENTION

Figure 1:
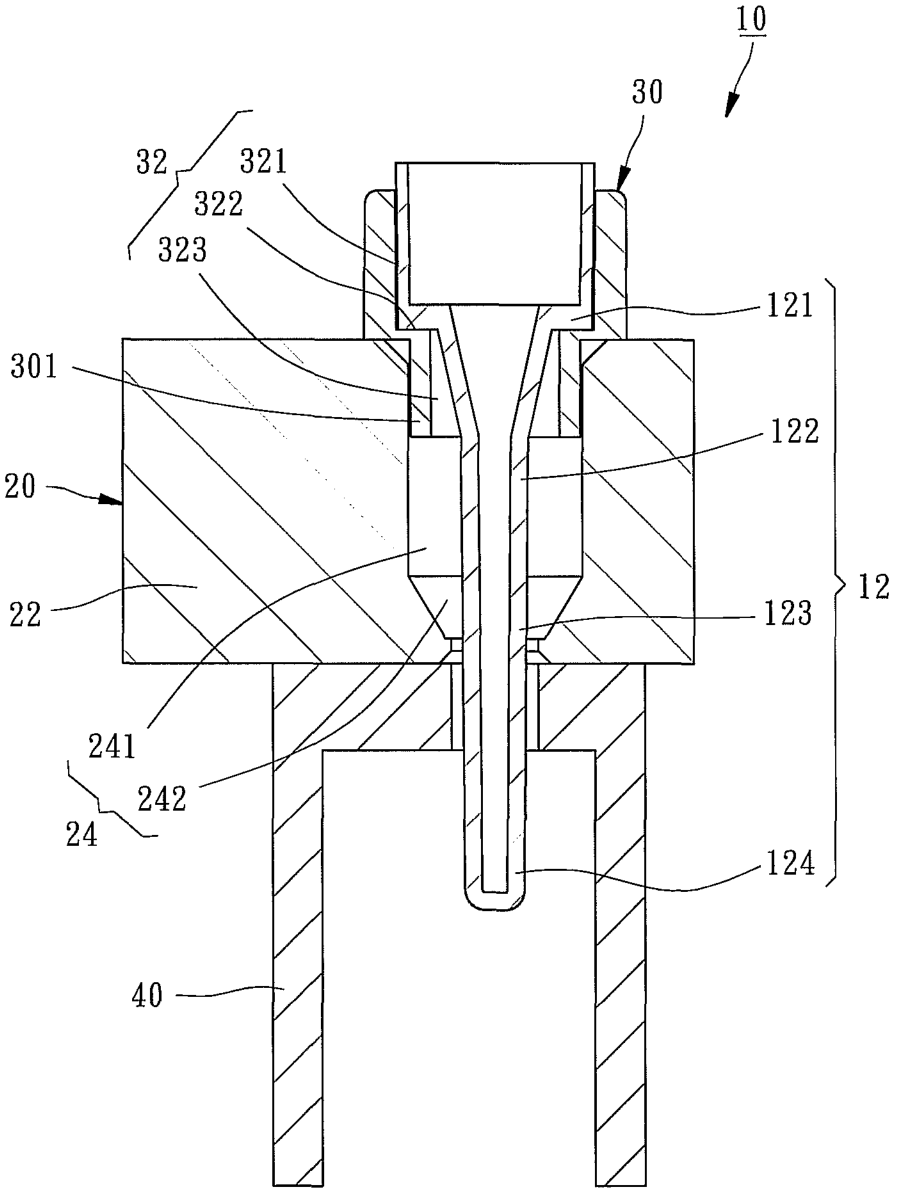
FIG. 1 is a schematic drawing showing an apparatus for insulated isothermal PCR according to a preferred embodiment of the present invention.

As shown in FIG. 1, an apparatus 10 for insulated isothermal PCR mainly comprises a heat sink 20 and a tube rack 30. The heat sink 20 includes a main body 22 provided with a through hole 24 for insertion of a test tube 12. The through hole 24 has a relatively big diameter section 241 and a relatively small diameter section 242 located below the relatively big diameter section 241. Because a middle section 123 and an upper section 122 of the test tube 12 are located inside the through hole 24 of the heat sink 20 and the heat sink 20 is made of a material having a high heat transfer coefficient, such as aluminum, the heat energy of the reaction mixture of PCR will be transferred through the ambient atmosphere to the heat sink 20 for heat dissipation efficiently, such that during the PCR process the temperature at the liquid level of the reaction mixture can be maintained at a degree of about 10-55° C., which is lower than the temperature suitable for performing the primer annealing step, thereby preventing the break of PCR due to high temperature at the reaction mixture level. In addition, the heat dissipation of the reaction mixture at the region corresponding to the relatively big diameter section 241 will be lower than that at the region corresponding to the relatively small diameter section 242. It is revealed by experiments that the configuration of the heat sink 20 provided by the present invention has a heat-dissipating effect helpful for conducting the insulated isothermal PCR.

In order to stably mount the test tube 12 in the heat sink 20, the tube rack 30 can be further provided on the heat sink 20. The tube rack 30 is provided with a receiving hole 32 for insertion of the test tube 12 to stably position the test tube 12, thereby preventing the outer wall surface of the test tube 12 from contacting the wall surface of the through hole 24 of the heat sink 20 so as to avoid that the temperature of the reaction mixture drops too quickly.

In practice, the receiving hole 32 of the tube rack 30 may be configured, in succession order from a top thereof toward a bottom thereof, a relatively big diameter section 321, a shoulder 322 and a relatively small diameter section 323, in which the shoulder 322 is adapted for stopping a shoulder 121 of the test tube 12 such that the test tube 12 can be stably positioned. In addition, a support seat 40 is provided below the heat sink 20. The bottom 124 of the test tube 12 is heated by a heat source (not shown in the drawings) to keep the temperature of the reaction mixture of PCR inside the bottom 124 in a range about 90° C. to 97° C.

Further, the bottom end 301 of the tube rack 30 is inserted into the through hole 24 of the heat sink 20, such that the tube rack 30 is stably mounted on the heat sink 20.

Furthermore, in the preferred embodiment of the present invention, the diameter of the relatively small diameter section 242 of the through hole 24 is configured to gradually and downwardly decrease. According to many experiments and modifications, it is found that using this configuration to dissipate heat can yield a highest reaction efficiency of PCR. The aforesaid experiments for PCR were conducted in seven different environmental temperatures ranging from 10° C. to 40° C. with a condition that the reaction mixture inside the bottom 124 of the test tube 12 was heated to 93° C. to 97° C. The temperature of the heat sink 20 measured ranges from 36° C. to 53° C., and the temperature at the reaction mixture level measured ranges from 36° C. to 53° C.; therefore, the PCR is performed smoothly.

Figure 2:
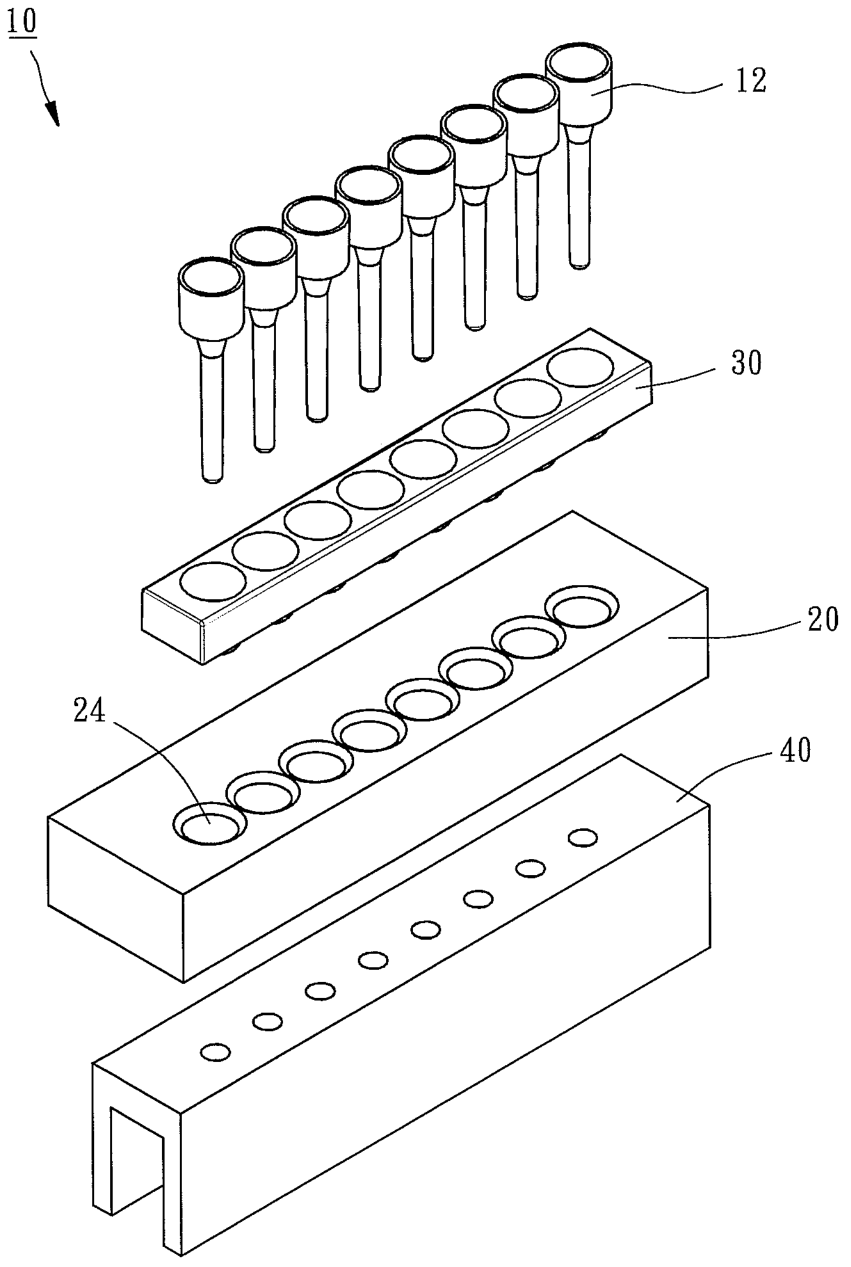
FIG. 2 is an exploded view of the apparatus for insulated isothermal PCR of the preferred embodiment of the present invention.

The invention being thus described, it will be obvious that the same may be varied in many ways. For example, as shown in FIG. 2, the heat sink 20 can be provided with a plurality of through holes 24 for holding a plurality of test tubes 12 for simultaneously performing polymerase chain reactions. Such variations are not to be regarded as a departure from the spirit and scope of the invention, and all such modifications as would be obvious to one skilled in the art are intended to be included within the scope of the following claims.

What is claimed is:

1. An apparatus for holding a test tube in which insulated isothermal polymerase chain reaction is performed, the apparatus comprising:

a heat sink having a main body provided with a through hole for insertion of an upper section and a middle section of the test tube; the heat sink being adapted to transit the heat energy at the upper section and the middle section of the test tube to ambient atmosphere while a bottom section of the test tube is heated; wherein the through hole has a relatively big diameter section and a relatively small diameter section located below the relatively big diameter section; and a tube rack mounted on the heat sink and provided with a receiving hole for insertion of the test tube such that an outer wall of the test tube is prevented from contacting a wall surface of the through hole of the heat sink.

2. The apparatus of claim 1, wherein the receiving hole of the tube rack includes, in succession order from a top of the receiving hole toward a bottom of the receiving hole, a relatively big diameter section, a shoulder for stopping a shoulder of the test tube, and a relatively small diameter section.

3. The apparatus of claim 1, wherein the tube rack has a bottom end inserted into the through hole of the heat sink.

4. The apparatus of claim 1, wherein the relatively small diameter section of the through hole of the heat sink has a diameter gradually downwardly decreasing.

5. The apparatus of claim 1, wherein the heat sink is made of metal.

* * * * *